United States Patent [19]

Hyde

[11] Patent Number: 4,530,579
[45] Date of Patent: Jul. 23, 1985

[54] ASTIGMATIC RULER AND METHOD OF USE THEREOF

[76] Inventor: Lawrence L. Hyde, 2900 Baltimore, Ste. 650, Kansas City, Mo. 64108

[21] Appl. No.: 529,485

[22] Filed: Sep. 6, 1983

[51] Int. Cl.³ .............................................. A61B 3/14
[52] U.S. Cl. .................................... 351/212; 351/247
[58] Field of Search ....................... 351/212, 211, 247

[56] References Cited

U.S. PATENT DOCUMENTS

| | | |
|---|---|---|
| 3,264,932 | 8/1966 | Hendricks . |
| 3,552,837 | 1/1971 | Volk . |
| 3,895,860 | 7/1975 | Townsley . |
| 3,972,602 | 8/1976 | Inns . |
| 4,157,859 | 6/1979 | Terry . |
| 4,159,867 | 7/1979 | Achatz et al. . |
| 4,256,385 | 3/1981 | Cohen et al. . |
| 4,426,141 | 1/1984 | Holcomb ............................ 351/212 |

Primary Examiner—Rodney B. Bovernick
Attorney, Agent, or Firm—Litman, Day and McMahon

[57] ABSTRACT

An astigmatic ruler for determining an amount of astigmatism associated with a cornea of a human eye by qualitative methods comprises a target member having a plurality of apertures therethrough. One of the apertures is circular and the remaining apertures are elliptical in shape. The elliptical apertures are associated with various incremental amounts of astigmatism. The target member is adapted to be positioned between the eye and an illuminated surgical microscope such that light is projected through a selected aperture and onto the eye. The amount of astigmatism associated with the eye is indicated when a selected aperture is presented to the eye and the aperture has a degree of ellipticity that generally balances the amount of astigmatism associated with the eye so that a generally circular image is reflected from the eye.

16 Claims, 11 Drawing Figures

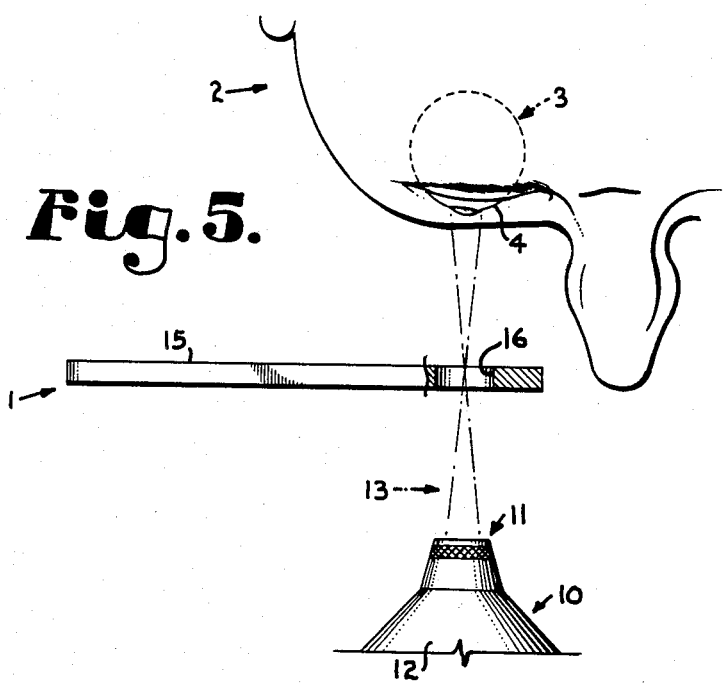
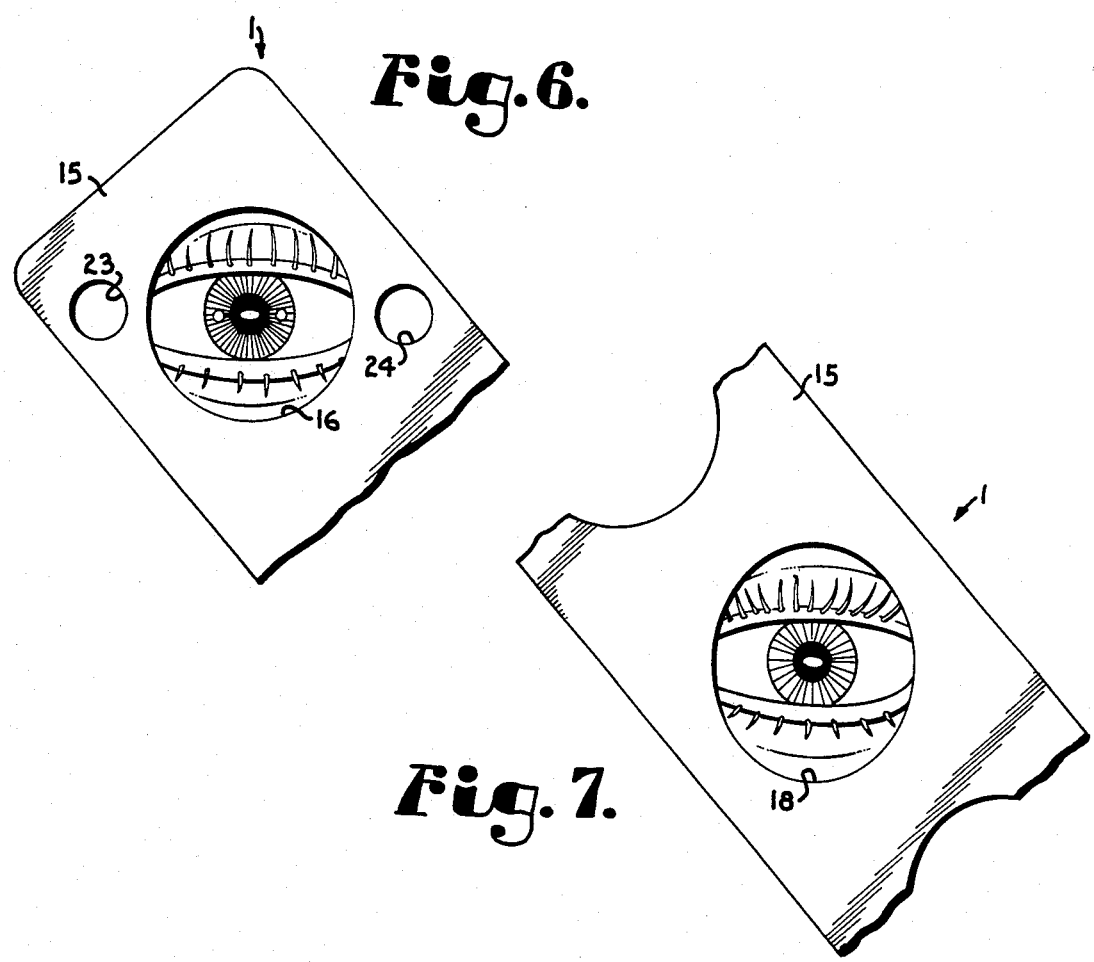

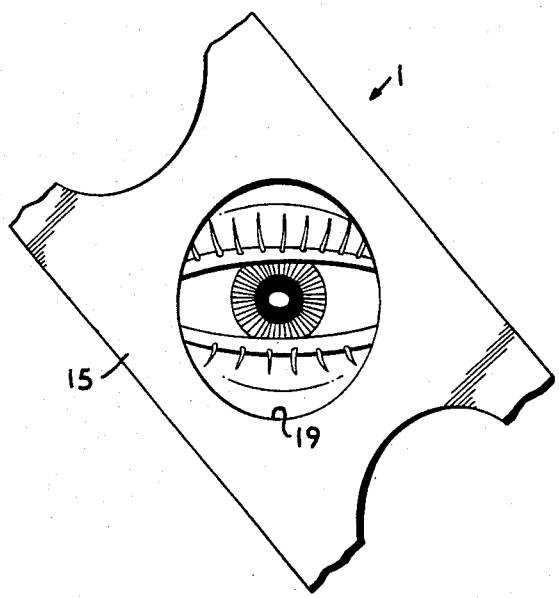
Fig.8.
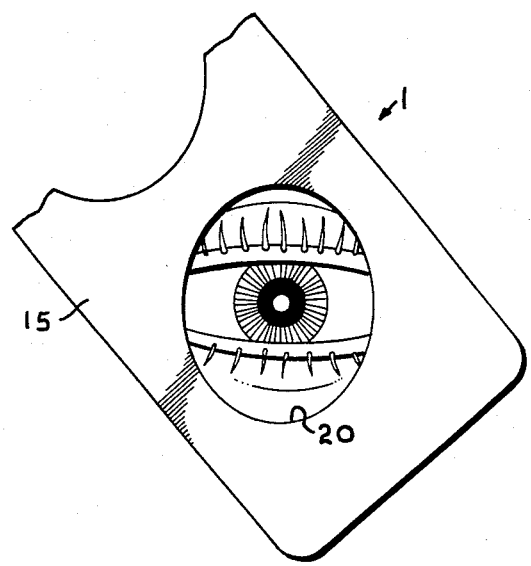
Fig.9.
Fig.10.
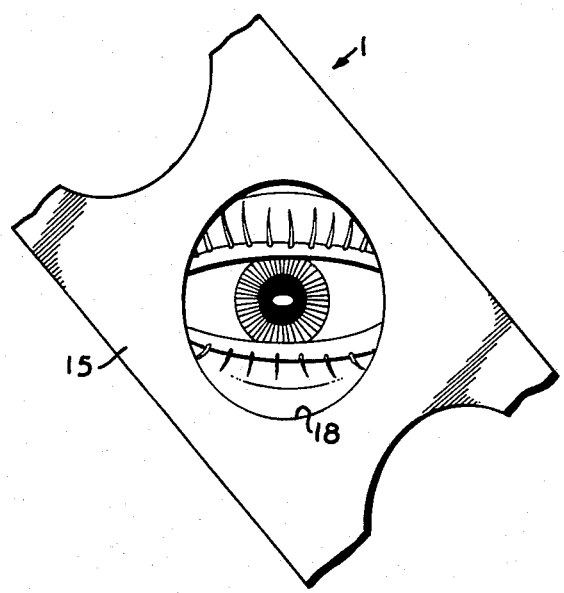
Fig.11.
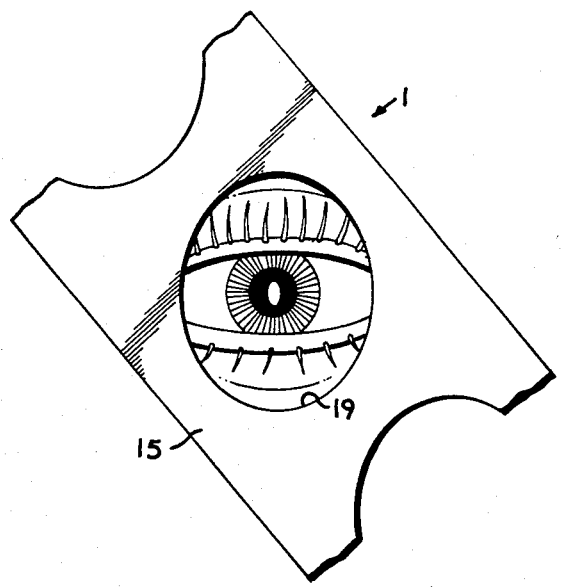

ASTIGMATIC RULER AND METHOD OF USE THEREOF

BACKGROUND OF THE INVENTION

This invention relates to ophthalmic instruments and, in particular, to such an instrument utilized in qualitatively determining an amount of astigmatism associated with a cornea of a human eye.

During certain surgery on the eye, for example a cataract operation, it is necessary to make an incision in the periphery of the cornea. After the operation, the incision must be sutured, which often creates a certain degree of astigmatism. Preferably, the the cornea should be reconfigured to its pre-operative shape or a shape having as little astigmatism as possible, so that any astigmatism associated therewith will not need correction or alternatively can be corrected fairly easily with corrective lenses. Perhaps the most well-known device that is used to ascertain measurements such as corneal astigmatism or curvature is the ophthalmometer. For example, Bausch and Lomb Corporation markets an ophthalmometer under the trademark "Keratometer". The ophthalmometer measures the anterior curvature of the cornea by interpretation of the measured size of a corneal image created by an object of known size located a fixed distance from the cornea. A ray of light is reflected onto the cornea and the resulting elliptical image is analyzed through a series of prisms. The typical ophthalmometer is a sophisticated, bulky, and extremely expensive piece of equipment. The device is not easily used in an operating room, due mainly to its bulk and the amount of time required to manipulate the device before quantitatively determining the corneal curvature.

Various other devices have been made to quantitatively determine the corneal astigmatism, or ellipticity associated with the cornea. These devices tend to be bulky and difficult to use in an operating room or tend to provide only extremely rough approximations. Some such devices are similar to ophthalmometers in that they use prisms to focus the reflected image in order to quantify the ellipticity. Certain measurement processes require extensive computer equipment to properly analyze the data developed thereby.

Another disadvantage that most of the complex prior art instruments have is that they require extensive manipulation to obtain the quantitative determination. Such manipulation is time consuming and tedious as the equipment is both bulky and somewhat fragile. These instruments are not easily sterilized and present a potential threat of contamination in the operating room.

Certain ophthalmic instruments rely on qualitative methods, but they are generally not accurate enough to provide significant information with respect to the amount of corneal astigmatism. Other devices have been too imprecise in giving comparative information and only provide an image of light shown through a circular opening. One such device that has been utilized is the circular spring portion of a safety pin.

Yet another disadvantage associated with certain of the known apparatus is that they require the degree of astigmatism to be estimated indirectly. That is, they do not allow the degree of astigmatism to be determined as an end point, but rather require the degree to be estimated based on the amount of ellipticity associated with the observed cornea.

OBJECTS OF THE INVENTION

The principal objects of the present invention are: to provide an ophthalmic instrument for qualitatively determining an amount of corneal astigmatism or ellipticity; to provide such an instrument which allows the amount of astigmatism to be qualitatively determined in a quick and simple manner with relative accuracy; to provide such an instrument which determines the amount of astigmatism as an end point, not by extrapolation; to provide such an instrument for astigmatic determination which presents the cornea with a series of elliptical light rings having a known diopter value associated therewith; to provide such an instrument which is easy to use; to provide such an instrument which can be used to quickly determine the amount of astigmatism, as compared to the quantitative instruments; to provide such an instrument which is easily sterilized and adapted to be hand held; to provide such an instrument which aids a surgeon in estimating the amount of induced astigmatism on a cornea that is being operated upon; to provide such an instrument which is economical to manufacture and particularly well adapted for the proposed usage thereof; and to provide a method for utilization of such an instrument.

Other objects and advantages of this invention will become apparent from the following description taken in conjunction with the accompanying drawings wherein are set forth, by way of illustration and example, certain embodiments of this invention.

SUMMARY OF THE INVENTION

An ophthalmic instrument, or astigmatic ruler, is provided to function in determining an amount of corneal astigmatism, or ellipticity, by qualitative methods. The instrument is of particular use during surgery on a human eye, such as cataract surgery. The surgeon must ordinarily make an incision in the periphery of the cornea, which must be sutured upon completion of the operation. The present invention allows the surgeon to quickly determine the ellipticity of the eye and to immediately adjust the incision closure. In particular, the astigmatic ruler can be used to estimate the amount of astigmatism induced on the cornea during surgery and suturing. Thus, the surgeon can reverse inadvertent overtightening of the sutures to avoid excessive induced astigmatic values, especially above five diopters.

The term diopter is known in the art and is expressed in units of reciprocal meters. The term diopter is used to denote the relative curvature and power of lenses, refracting surfaces, and other optical systems. As used herein, the term astigmatism refers to corneal astigmatism, which is a refractive defect that prevents the focusing of sharp, distinct images.

The astigmatic ruler includes an elongate bar or target member, which has a plurality of target apertures therethrough. The first target aperture is generally circular in shape, while the remaining target apertures are elliptical and directly associated with various incremental amounts of astigmatism which are predetermined before use of the ruler.

The target member is used with a light source, such as an illuminated operating microscope, and is positioned between the eye and the light source. The target member is selectively positioned between the eye and the light source so that light passes through a selected target aperture onto the eye, thereby forming a virtual image which is observable on the cornea. The shape of the virtual image depends on the optical properties of the cornea and the configuration of the selected target aperture.

The astigmatic ruler is generally utilized to determine the amount of corneal astigmatism by a user noting when the selected aperture which is presented to the eye has an associated amount of ellipticity directly related to the amount of astigmatism associated with the cornea so as to form a predetermined pattern of the virtual image. In particular, the virtual image will appear circular when the degree of ellipticity associated with the selected aperture is equal to the degree of ellipticity associated with the astigmatic cornea and the respective major axes of the ellipses associated with the aperture and the cornea are generally perpendicular to one another.

When the circular target aperture is used, a virtual image is formed on the eye that generally indicates the shape of the cornea. The circular target aperture can be considered to correspond to a zero amount of astigmatism. That is, when a light beam is projected through the circular aperture onto the eye with a resulting circular virtual image or visible reflection, then the cornea is said to have no astigmatism associated therewith. The target member has two light reflex openings therethrough, which are diametrically opposed to each other and located adjacent the circular target aperture. The elliptical target apertures are arranged along the target member in order of increasing degree of ellipticity in generally equal increments, with the aperture having the lowest degree of ellipticity positioned next to the circular target aperture. Additionally, the elliptical target apertures are aligned such that respective major axes thereof are parallel to one another, and perpendicular to an imaginary line extending through the centers of the light reflex openings. The axes of the ellipses of the target apertures are also generally aligned at about 45 degrees relative to a longitudinal axis of the target member to facilitate use of the device by the physician.

The circular target aperture and the light reflex openings are utilized to properly align the astigmatic ruler during use. The ruler is positioned between the cornea and the light source, with the circular aperture generally coaxially aligned with the light source. The ruler is adjusted to reflect a centered or uniform ring of light onto the cornea. A virtual image generally indicating the shape of the cornea will appear on or reflected from the cornea. The ruler is aligned such that two light reflexes associated with the light reflex openings appear near opposite ends of the major axis of the cornea. The alignment of the elliptical target apertures allows them to be presented to the cornea such that the major ellipse axes of each are in perpendicular relationship to one another and the ruler is movable linearly in the same plane to present different target apertures above the eye in proper perpendicular orientation.

In particular, the ruler is subsequently moved to present the first elliptical target aperture to the cornea. The associated virtual image will appear less elliptical than the virtual image of the circle if the cornea has an astigmatism greater than the ellipticity of that (first) target aperture. If the target aperture has less ellipticity than the cornea then the major axis of the virtual image will align with the minor axis of the cornea and, when the aperture has the same ellipticity as the cornea the virtual image will appear circular. Subsequent elliptical target apertures, in order of increasing ellipticity, are presented to the cornea until the virtual image, previously aligned with the major axis of the cornea, reverses to an ellipse appearing to be perpendicularly positioned with respect to the initial virtual image and aligned with the minor axis of the cornea. Such reversal indicates that the associated amount of astigmatism has been surpassed, and the ruler is then moved back and forth between the previously presented elliptical target apertures until it is apparent that one of the apertures affects the virtual image such that it appears to be circular or nearly circular, or alternatively that the circular image appears to be located between two adjacent apertures. The elliptical target aperture producing this circular virtual image is associated with a certain amount of astigmatism, which amount of astigmatism corresponds to the approximate qualitatively determined amount of astigmatism of the cornea.

If the amount of astigmatism is between two of the preselected amounts of astigmatism corresponding to the elliptical target apertures, the amount of astigmatism may be interpolated by observing the two elliptical target apertures that produce nearly round virtual images and subsequently determining either that one produces an image which is closer to circular or that the value is intermediate the two apertures if the ellipses of both images have approximately equal ellipticity.

The drawings constitute a part of this specification and include exemplary embodiments of the present invention and illustrate various objects and features thereof.

BRIEF DESCRIPTION OF THE DRAWINGS

FIG. 5 shows a reduced and fragmentary side elevational view of the ruler coaxially having an aperture thereof aligned between the patient's eye and a lens of an operating microscope projecting a light beam through the aperture, with portions removed to show detail thereof.

FIG. 6 is an enlarged and fragmentary top view of the ruler and eye showing a circular aperture thereof positioned over the eye and with virtual images of the circular aperture and two light reflex openings shown on a cornea of the eye.

FIG. 7 is an enlarged and fragmentary top view of an elliptical target aperture of the ruler and eye, showing the virtual image of the elliptical target aperture as affected by the curvature of the cornea.

FIG. 8 is an enlarged and fragmentary top view of the ruler and eye showing another elliptical target aperture with the virtual image associated therewith.

FIG. 9 is an enlarged and fragmentary top view of the ruler and eye showing another elliptical target aperture and its associated virtual image, which is shown as circular.

FIG. 10 is an enlarged and fragmentary top view of the ruler and eye showing the virtual image of one of the elliptical target apertures, which virtual image is generally horizontally aligned.

FIG. 11 is an enlarged and fragmentary top view of the ruler and eye showing the virtual image associated with the next succeeding (with respect to FIG. 10)

Figure 1:
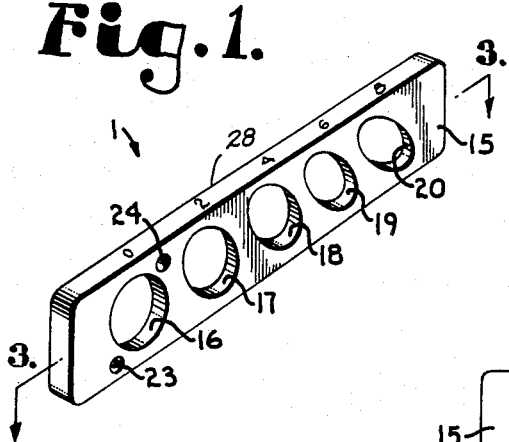
FIG. 1 is a perspective view of an astigmatic ruler according the present invention.

elliptical target aperture, which virtual image is generally vertically aligned.

It is noted that certain features, such as size or shape of the virtual image may have been exaggerated in certain of the Figures in order to better detail certain features for purposes of understanding.

DETAILED DESCRIPTION OF THE INVENTION

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally indicates an astigmatic ruler embodying the present invention. The ruler 1 is adapted to be utilized for qualitatively determining an amount of corneal astigmatism of a patient 2. The patient 2 has an eye 3 that has a cornea 4, iris 5, and pupil 6.

As illustrated in FIG. 5, the ruler 1 is adapted to be positioned between the patient's eye 3 and an operating microscope 10 having a viewing lens 11 and a light source 12, the light being indicated by broken lines numbered 13.

The ruler 1 includes an elongate target member, such as bar 15. As illustrated, the bar 15 is a relatively thin aluminum block. The bar 15 has a plurality of target apertures therethrough, such as a circular target aperture 16, and elliptical target apertures 17, 18, 19 and 20.

A suitable size for the ruler 1 has been found to be approximately four inches long by three-quarters of an inch wide by three sixteenths of an inch deep. The ruler 1 is preferably surfaced with a non-reflective coating except for the apertures.

Figure 2:
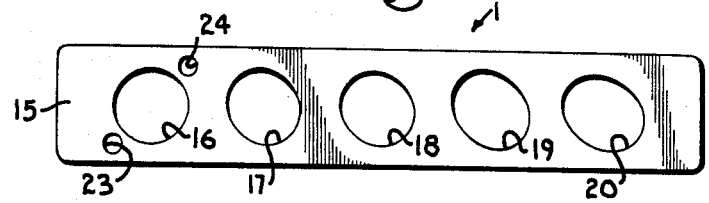
FIG. 2 is a top view of the ruler.
Figure 3:
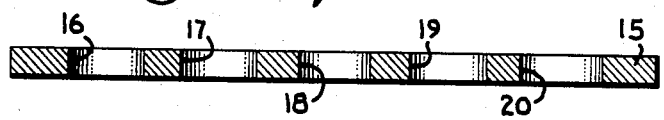
FIG. 3 is a cross-sectional view of the ruler taken along line 3—3 of FIG. 1.
Figure 4:
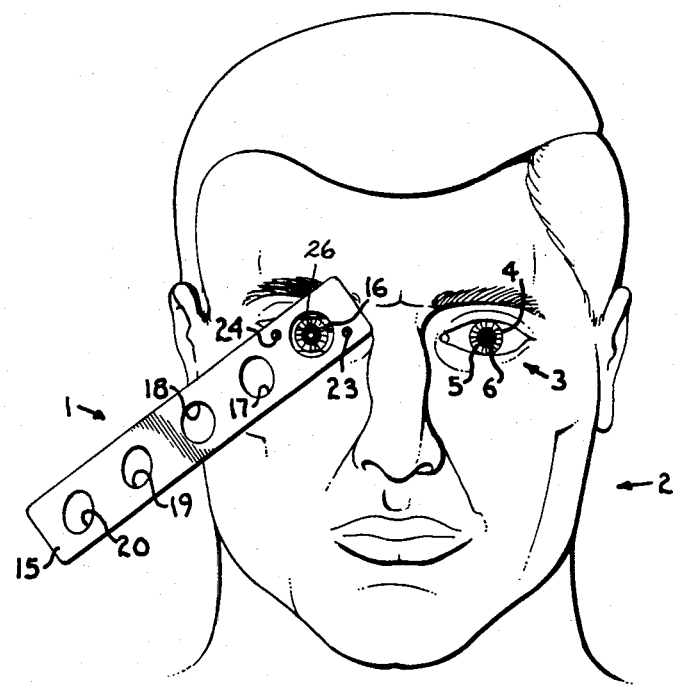
FIG. 4 is a top view of the ruler on a reduced scale and shows a circular aperture of the ruler aligned with an eye of a human patient.

As illustrated in FIG. 2, the circular target aperture 16 is the first aperture through the bar 15, as viewed from the left. The bar 15 has two light reflex openings 23 and 24 therethrough. The reflex openings 23 and 24 are positioned adjacent the circular target aperture 16, on diametrically opposed sides thereof and positioned such that a line passing through the center of both openings 23 and 24 is generally at approximately 45 degrees to the main axis of the bar 15. When the bar 15 is positioned between the light source 12 and the cornea 4, a selected aperture may be coaxially aligned with the light source so that a light beam projected therefrom is allowed to impinge upon the cornea 4 through the selected aperture. For example, the circular target aperture 16 may be so aligned, whereupon a virtual image 26 is seen on the surface of the cornea 4. The virtual image 26 has a shape which results from the interaction of the optical properties of the cornea 4 and the configuration of the selected target aperture. The virtual image 26 produced when the circular target aperture 16 is presented to the cornea 4 generally indicates the shape of the cornea 4. When the cornea 4 is astigmatic, it is elliptical in shape, having a major and a minor axis. Thus, the virtual image 26 associated therewith has a major and a minor axis when the light beam striking the cornea 4 is basically circular.

The elliptical target apertures 17, 18, 19 and 20 have various degrees of ellipticity. Each elliptical target aperture corresponds to a preselected incremental amount of astigmatism. As illustrated, the respective elliptical target apertures 17, 18, 19, and 20 correspond to 2, 4, 6, and 8 diopters of astigmatism respectively. The circular target aperture 16 corresponds to a zero amount of astigmatism. The bar 15 may be provided with appropriate astigmatism-noting indicia 28.

In principal, the ellipticity of the elliptical target apertures 17, 18, 19, and 20 cooperates with the ellipticity of the astigmatic cornea to cancel the respective ellipses when the selected aperture has a degree of ellipticity which is in general equal to the ellipticity of the astigmatic cornea and they are properly positioned relative to one another. More specifically, when an elliptical target aperture is presented to the ellipse of the cornea at a 90 degree angle, a circular virtual image will be produced when the ratios of the respective major to minor axes of the selected target aperture and the astigmatic cornea are equal.

Thus, it is important for the elliptical target apertures 17, 18, 19, and 20 to be presented to the cornea 4 such that the respective major axes thereof are generally perpendicular. The light reflex openings 23 and 24 are aligned in a specified relation with the major axes of the elliptical target apertures 17, 18, 19, and 20. That is, the elliptical target apertures 17, 18, 19, and 20 are aligned on the bar 15 such that their major axes are perpendicular to an imaginary line projected through centers of the light reflex openings 23 and 24. This arrangement allows the elliptical target apertures 17, 18, 19, and 20 to be presented in the proper orientation to the cornea 4. The orientation is accomplished by presenting the circular target aperture 16 and the light reflex openings 23 and 24 to the cornea 4 with the light source 12 therebehind. The virtual image 26 in the cornea 4 associated with the circular aperture 16 generally indicates the shape of the cornea 4, and the bar 15 is properly aligned when the light reflexes associated with the light reflex openings 23 and 24 are located at either end of the major axis of the virtual image 26. It is noted that the light reflex openings 23 and 24 could be aligned otherwise about the aperture 16 or another aperture 17, 18, 19 or 20 provided that it is understood where the corresponding light reflexes should appear relative to the eye 3.

As will be further discussed below, the elliptical target apertures 17, 18, 19, and 20 are generally arranged along the bar 15 in increasing order in terms of amount of associated astigmatism, from the circular target aperture 16.

In use, the ruler 1 is placed in spaced relationship above the eye 3, with a light source, such as from the operating microscope 10, located above the ruler 1. It has been found that the ruler 1 is preferably held approximately 2 centimeters above the cornea 4.

The bar 15 is initially positioned with the circular target aperture 16 coaxially aligned with the light source 12, thereby projecting light through the aperture 16 onto the cornea 4. This position is illustrated in FIG. 6. The virtual image 26 of the cornea is noted as a visually perceptible reflection of the light over the iris 5. The bar 15 should be tilted to reflect a uniform ring of light, which forms the virtual image 26. The virtual image 26 may be varied in size by raising or lowering the bar 15.

The bar 15 is rotated about an axis through the center of the aperture 16 until the light reflexes associated with the light reflex openings 23 and 24 appear at either end of the major axis of the virtual image 26 and at opposite ends of major axes of the eye 3 or the elliptical corneal reflex (See FIG. 6). It is noted that the major axis generally represents a flat meridian of the cornea 4.

Once properly aligned, the bar 15 is moved linearly in the same plane, thereby ensuring that succeeding and preceding apertures are aligned generally perpendicularly with respect to the astigmatic cornea 4. The operator observes the virtual image 26 as the bar 15 is moved from one elliptical target aperture to another. The elliptical target apertures 17, 18, 19, and 20 are arranged in order of increasing amount of associated astigmatism. The illustrated target apertures 17, 18, 19, and 20 correspond to 2, 4, 6, and 8 diopters of astigmatism, respectively. If the cornea 4 is astigmatic, then as the bar 15 is moved, the virtual image 26 should become progressively less elliptical in shape, as illustrated in FIGS. 6, 7 and 8 showing sequentially more elliptical apertures, and may eventually reverse to an ellipse that is generally perpendicular to the initial ellipse associated with the virtual image 26 of the circular target aperture 16. With respect to the astigmatism associated with the eyes shown in FIGS. 6 through 9, the ellipse of the virtual image does not become aligned at 90° to the ellipse of the virtual image associated with aperture 16, but rather finally becomes circular when the light beam is shown through the last aperture 20 having an 8 diopter ellipse associated therewith. The eye shown in FIGS. 10 and 11 is a different eye from that shown in FIGS. 4 through 9 and the astigmatism of the eye shown in FIGS. 10 and 11 is such that the virtual image in that eye would be circular if a light beam were shown through an aperture having an ellipticity between that of apertures 18 and 19 onto the eye that is between 4 and 6 diopters. The amount of astigmatism associated with that eye may be estimated by an interpolation process, which is detailed below.

Once the ellipse of the virtual image 26 has reversed, the bar 15 is moved back and forth between the elliptical target apertures 17, 18, 19, and 20 until the operator qualitatively determines which of the target apertures produces the virtual image 26 which is most nearly circular, if not circular. FIG. 9 illustrates a circular virtual image 26 produced when the ellipticity of target aperture 20 cancels the ellipticity of the cornea. Because the target apertures each correspond to a preselected amount of astigmatism, the operator can correlate his observation of the circular virtual image 26 to an amount of astigmatism. With this information at hand during an operation, such as for cataracts, the surgeon can take corrective action to adjust the sutures of the corneal incision closure within an acceptable tolerance range of induced astigmatism.

Referring again to FIGS. 10 and 11, the amount of astigmatism associated with the illustrated eye is between 4 and 6 diopters and an interpolation process is possible, although normally this knowledge will suffice to execute a suturing correction to reduce the astigmatism. As illustrated, the elliptical target apertures 17, 18, 19, and 20 correspond to specific even numbers of diopters (i.e. 2, 4, 6, and 8 diopters respectively). Thus, one can interpolate an odd number or fractional amount of diopters of astigmatism. This interpolation is achieved by observing that two of the virtual images 26 associated with the target apertures appear nearly circular, but neither is truly circular, as shown in FIGS. 10 and 11. Upon closer observation it should be noticed that the virtual images 26 are in fact shifting upon back and forth movement. It should also be observed that the virtual images 26 are at right angles with respect to one another, thus indicating that the proper degree of ellipticity falls between them. As illustrated, it would be estimated that the astigmatism associated with the eye is about 5 diopters.

Specifically, as discussed above, a circular virtual image 26 is produced when the ratios of the respective major axes to the minor axes of the elliptical target aperture and the astigmatic cornea are equal. If the ellipticity amount of the eye is not found exactly at one aperture on the ruler 1, it will be normally observed that two adjacent elliptical target apertures will have associated virtual images 26 which appear to be perpendicular. This shifting of ellipses is illustrated in FIGS. 10 and 11. The operating surgeon can then qualitatively interpolate between the two adjacent elliptical target apertures, and estimate the amount of astigmatism. Ellipticity values greater than shown on the ruler 1 require readjustment of the sutures and a retesting of the eye 3 to determine if the ellipticity is then within a suitable range not requiring further correction during the operation.

If the first elliptical target aperture 17 produces a virtual image 26 which is perpendicular to the original virtual image 26, it will be apparent that a relatively small amount of astigmatism is involved. This would indicate that between zero and two diopters of astigmatism are present in the cornea 4. Thus, the circular target aperture 16 can be used to determine the amount of associated astigmatism. Also, if the virtual image 26 has not reversed by the time the final elliptical target aperture 20 is presented to the eye, the amount of astigmatism is greater than that associated with aperture 20. After the corrective action has been taken, the ruler 1 can then again be utilized to determine the present amount of astigmatism.

Although the amount of astigmatism associated with the selective elliptical target apertures 17, 18, 19, and 20 is a matter of choice, it is anticipated that most users would choose apertures having associated amounts of astigmatism between zero and eight diopters. Additionally, more elliptical target apertures could be added to the ruler 1 by extending the bar 15.

During use, if the elliptical virtual image 26 appears oblique, the ruler 1 has been inadvertently rotated and must be realigned, using the light reflex openings 23 and 24.

It is to be understood that while certain forms of the present invention have been illustrated and described herein, it is not to be limited to the specific forms or arrangement of parts described and shown.

What is claimed and desired to be secured by Letters Patent is as follows:

1. An instrument for the determination of the degree of astigmatism associated with an eye; said instrument comprising:
   (a) a bar being suitable for manipulation by an observer above the eye for which the degree of astigmatism is to be tested;
   (b) a plurality of apertures passing through said bar and adapted to have a light beam pass therethrough and into the eye to be tested; and
   (c) each of said apertures being defined by respective ellipses, each having an ellipse having a different degree of ellipticity associated therewith, such that, when a major axis of the ellipse of the particular aperture associated with the astigmatism of the eye to be tested is placed above and generally perpendicular to a major axis of the cornea of the eye to be tested, a light beam passing through such particular aperture will be reflected by the eye so as to appear as a predetermined and recognizable pattern to the observer.

2. An ophthalmic instrument for use in qualitatively determining an amount of astigmatism associated with a human eye and comprising:
 (a) a target member;
 (b) said target member having a plurality of apertures therethrough; each of said apertures having a different degree of ellipticity associated therewith; the degree of ellipticity of each of said apertures being related to a predetermined amount of astigmatism in an eye such that, when a light is passed through the particular aperture related to the amount of astigmatism of that particular eye, then the reflection of that light beam in the eye will appear as a recognizable and predetermined pattern;
 (c) said target member being adapted to be positioned between the eye for which the amount of astigmatism is derived to be known and a light source for providing the light beam; said target member being selectively positionable between the eye and the light source so as to allow the light source to project through a single selected aperture onto said eye; and
 (d) wherein said instrument may be moved to place different apertures above the eye so that the light beam passes through the apertures and is reflected in the eye such that a user can qualitatively determine the aperture having the degree of ellipticity most closely associated with the amount of astigmatism associated with said eye by the reflection in the eye.

3. The instrument set forth in claim 2 wherein:
 (a) a virtual image is formed on the cornea when light is projected through a selected aperture onto said eye; and
 (b) each of said apertures have incremental degrees of ellipticity as compared with each other and are associated with various incremental amounts of astigmatism such that said virtual image appears substantially circular when a major axis of said selected aperture is generally perpendicularly aligned with a major axis associated with the eye and the degree of ellipticity associated with said selected aperture generally corresponds to the amount of asigmatism associated with the eye.

4. The instrument set forth in claim 3 wherein:
 (a) one of said apertures is substantially circular and said virtual image associated therewith generally indicates the shape of the cornea.

5. The instrument set forth in claim 4 wherein:
 (a) said target member has a light reflex opening therethrough and located adjacent one of said apertures; said light reflex opening being positioned such that, when said elliptical apertures are positioned to be presentable to the cornea such that respective major axes thereof are substantially perpendicular to said major axis of the corneal virtual image and light is projected through said reflex opening and onto the eye, a virtual image associated with said reflex opening is positioned along the major axis of the cornea.

6. The instrument set forth in claim 2 wherein:
 (a) said instrument is adapted to be hand held.

7. The instrument as set forth in claim 2 wherein:
 (a) said apertures are linearly spaced along said bar; the first of said apertures being round and each subsequent of said apertures being a specific incremental amount different in ellipticity from adjacent apertures.

8. The instrument according to claim 7 wherein:
 (a) the incremental amount of difference in ellipticity between apertures is approximately two diopters.

9. An ophthalmic instrument for indicating by qualitative methods an amount of astigmatism associated with a cornea of an eye by presenting a series of ellipses having known and varying degrees of ellipticity to the cornea; said instrument comprising:
 (a) a bar;
 (b) said bar having a plurality of apertures therethrough, each with an associated different degree of ellipticity;
 (c) a light source for selectively projecting a beam of light through various of said apertures and onto the cornea whereby a virtual image of each of the apertures as affected by the cornea is selectively produced and observed on the cornea; and
 (d) such that, when the particular aperture having a degree of ellipticity generally corresponding to the amount of astigmatism associated with the cornea is presented to the cornea, the virtual image produced on the cornea is generally circular.

10. The instrument set forth in claim 9 wherein:
 (a) said apertures each have a different degree of ellipticity and have a major axis and a minor axis;
 (b) there is a major axis and a minor axis associated with the cornea of the eye; and
 (c) said apertures are shaped so that, when a selected of said apertures is positioned relative to the cornea such that the major axis of the cornea is generally perpendicular to the major axis of the selected aperture, said apertures cooperate with the astigmatism of the eye to cancel the projected elliptical virtual image so as to produce a circular image when the ratios of the respective major and minor axes of the ellipse of the eye and of a selected aperture are generally equal.

11. The instrument set forth in claim 10 wherein:
 (a) said apertures of different elliptical configurations are aligned on said bar so that linear movement of said bar in the same plane properly aligns succeeding and preceding ellipses with respect to the astigmatic cornea.

12. The instrument set forth in claim 11 wherein:
 (a) each aperture has a degree of ellipticity which is approximately equally different from the degree of ellipticity of adjacent apertures.

13. An ophthalmic instrument for qualitatively determining an amount of corneal astigmatism associated with a human eye by projecting a series of ellipses of known ellipticity onto a cornea of the eye and noting the shape of the reflected virtual image, said instrument comprising:
 (a) an elongated target member;
 (b) said target member having a series of target apertures therethrough;
 (c) an operating microscope with a light source for projecting light sequentially through selected one of said target apertures and onto the cornea whereby a virtual image of the target aperture as affected by the cornea is produced on the cornea;

said microscope having a lens for observing said virtual image through said selected target aperture;

(d) a first of said target apertures being substantially circular, such that the virtual image corresponding thereto generally indicates the shape of the cornea;

(e) said target apertures after said first aperture being elliptical in shape and having a specific and predetermined degree of ellipticity associated therewith; each of said elliptical target apertures being directly associated with a different and preselected incremental amount of astigmatism of an eye; each of said elliptical target apertures having a major axis and a minor axis;

(f) said target member having a pair of light reflex openings therethrough and located near said circular target aperture on diametrically opposed sides thereof; said light reflex openings being relatively smaller in diameter than said circular target aperture and adapted to allow projection of light therethrough when positioned over the cornea; said openings being alignable with opposite ends of a major axis of the cornea so as to properly align the target member so that the major axis of said aperture is perpendicular to a major axis of the cornea;

(g) said elliptical target apertures being generally linearly arranged along said target member away from said circular target aperture and in order of increasing amount of associated astigmatism;

(h) said elliptical target apertures being aligned such that:
  (1) respective major axes thereof are parallel to each other and perpendicular to an imaginary line projected through respective centers of said light reflex openings; and
  (2) linear movement of said target member in the same plane presents succeeding and preceding elliptical target apertures directly above the astigmatic cornea in generally perpendicular relation with respect to respective major axes thereof; and (i) said target apertures tending to cooperate with the astigmatic properties of the cornea to generally cancel the ellipticity of the projected virtual image, such that said virtual image appears circular when the ratios of respective major and minor axes of said target apertures and the astigmatic cornea are generally equal; the ellipticity of the aperture being closest to producing a circular virtual image being directly related to and indicating the amount of astigmatism associated with the cornea.

14. A method of qualitatively determining an amount of astigmatism associated with a cornea of an eye having a major axis, comprising the steps of:
  (a) placing in spaced relationship to the eye a target member having a plurality of apertures therethrough, each of said apertures being defined by various elliptical configurations, each different from the other and having a degree of ellipticity and a major axis associated therewith;
  (b) positioning a light source such that said target member is between said light source and said eye;
  (c) selectively aligning and positioning said target member such that said light source projects light through the various apertures individually onto the eye and such that the major axis of each aperture is generally perpendicular to the major axis of the cornea of the eye;
  (d) for each aperture, observing the reflected pattern in the eye;
  (e) noting the aperture associated with the reflected pattern appearing most nearly circular; and
  (f) qualitatively determining the amount of astigmatism of the eye based on a predetermined value of such astigmatism associated with the noted aperture producing the reflected pattern appearing most nearly circular.

15. The method set forth in claim 14, further comprising the steps of:
  (a) noting the two apertures that are associated with reflected patterns appearing most nearly circular;
  (b) shifting rapidly between said two reflected patterns appearing most nearly circular and noting that one is slightly oval in a horizontal orientation and the other is slightly oval in a vertical orientation;
  (c) determining by qualitative interpolation the approximate amount of astigmatism of the eye based on interpolation between the predetermined values of astigmatism associated with said two reflected patterns appearing most nearly circular.

16. The method as set forth in claim 14 further including the steps of:
  (a) providing a reflex opening adjacent one of said apertures and being generally aligned such that an imaginary line passing through the reflex opening and the adjacent aperture has a particular predetermined configuration associated with positioning the adjacent aperture relating to the eye; and during positioning of the target over the eye;
  (b) aligning said imaginary line with the preselected configuration relative to the cornea when directing light through the aperture adjacent the opening.

* * * * *